United States Patent [19]
Salmon et al.

[11] Patent Number: 5,458,585
[45] Date of Patent: Oct. 17, 1995

[54] TRACKING TIP FOR A WORK ELEMENT IN A CATHETER SYSTEM

[75] Inventors: Stephen M. Salmon, Sunnyvale; John R. McKenzie, San Francisco; David A. White, San Jose, all of Calif.

[73] Assignee: Cardiovascular Imaging Systems, Inc., Sunnyvale, Calif.

[21] Appl. No.: 98,549

[22] Filed: Jul. 28, 1993

[51] Int. Cl.[6] ............................................. A61M 25/00
[52] U.S. Cl. ................ 604/280; 604/264; 128/662.06; 128/772
[58] Field of Search .................. 128/772, 656–658, 128/662.06; 604/22, 95, 264–266, 280; 606/167–171

[56] References Cited

U.S. PATENT DOCUMENTS

| | | | |
|---|---|---|---|
| 4,771,788 | 9/1988 | Millar | 128/661.09 |
| 4,811,743 | 3/1989 | Stevens | 128/772 |
| 4,984,581 | 1/1991 | Stice | 128/772 |
| 5,029,588 | 7/1991 | Yock et al. | 128/662.06 |
| 5,108,411 | 4/1992 | McKenzie | 606/159 |
| 5,174,295 | 12/1992 | Christian et al. | 128/662.06 |
| 5,201,315 | 4/1993 | Griffith | 128/662.06 |
| 5,201,316 | 4/1993 | Pomeranz et al. | 128/662.06 |
| 5,207,229 | 5/1993 | Winters | 128/772 |
| 5,226,421 | 7/1993 | Frisbie et al. | 128/662.04 |
| 5,242,394 | 9/1993 | Tremulis | 604/95 |

FOREIGN PATENT DOCUMENTS

| | | | |
|---|---|---|---|
| 8907419 | 8/1989 | WIPO | 128/662.06 |

*Primary Examiner*—Corrine M. Maglione
*Attorney, Agent, or Firm*—Townsend and Townsend and Crew

[57] ABSTRACT

The claimed invention provides an improved tracking tip for use with a work element in a catheter system having a flexible tubular catheter body. Use of a tracking tip according to the present invention will facilitate advancement of the work element within the catheter body and will substantially eliminate the possibility that the work element will puncture the catheter body. Preferred embodiments will comprise a wire coil and will often include a rounded end member, which may be in the form of a solder ball, at the distal tip of the wire coil. In some embodiments, the rounded end member may be coated with a lubricant or a suitable non-stick material to further improve tracking of the work element within the catheter body.

26 Claims, 7 Drawing Sheets

TRACKING TIP FOR A WORK ELEMENT IN A CATHETER SYSTEM

BACKGROUND OF THE INVENTION

1. Field of the Invention

The present invention provides an improvement for use in a catheter system having a work element coupled to a drive shaft disposed within a flexible tubular catheter body. More particularly, the present invention provides an improved tracking tip to facilitate movement of the work element within the catheter body and to minimize the risk of the work element puncturing the wall of the catheter body.

2. Description of the Background Art

Arteriosclerosis, also known as atherosclerosis, is a common human ailment arising from the deposition of fatty-like substances, referred to as atheromas or plaque, on the walls of blood vessels. Such deposits occur in both the peripheral blood vessels, which feed the limbs of the body, and the coronary vessels, which feed the heart. When deposits accumulate in localized regions of a blood vessel, stenosis, or narrowing of the vascular channel, occurs. Blood flow is restricted and the person's health is at serious risk.

Numerous approaches for reducing and removing such vascular deposits are known, including balloon angioplasty, in which a balloon-tipped catheter is used to dilate a region of atheroma; atherectomy, in which a blade or cutting bit is used to sever and remove the atheroma; spark gap reduction, in which an electrical spark burns through the plaque; and laser angioplasty, in which laser energy is used to ablate at least a portion of the atheroma. In order to facilitate treatment of the stenosis, it is often desirable to obtain a visual image of the interior of the blood vessel within the region of interest. Catheters having imaging elements such as ultrasonic transducers are often used to obtain these images.

In many cases, catheter systems having imaging or interventional devices will include a rotatable drive shaft disposed within the flexible catheter body. Catheters of this type will have some type of work element fixed to the distal end of the drive shaft. In imaging systems, the work element is typically an ultrasonic transducer or a movable mirror associated with an ultrasonic transducer.

An exemplary catheter system having a rotating ultrasonic transducer coupled to a drive shaft is disclosed in U.S. Pat. No. 4,794,931, the disclosure of which is incorporated herein by reference. In this system, a drive shaft disposed within a flexible tubular catheter body is used to rotate an ultrasonic transducer about an axis parallel to the catheter body. The ultrasonic transducer is thereby caused to scan a region of the blood vessel in a plane normal to the catheter body.

Another catheter system, which may include an imaging or interventional work element connected to a rotating drive shaft, is disclosed in U.S. Patent application Ser. No. 07/975,769, filed on Nov. 13, 1992, the disclosure of which is incorporated herein by reference. This "common lumen" catheter system includes a proximal region having multiple lumens for carrying a guidewire and various work elements and a reduced profile single lumen distal region. A catheter system of this type is advantageous in that the common lumen distal region, having a narrower profile, is able to enter into more constricted areas than would otherwise be possible.

A catheter of the type having a common distal lumen is used as follows. First, a guidewire is advanced into the patient until it lies within a region of interest, typically a region of stenosis within the blood vessel. After the guidewire is positioned, the proximal end of the guidewire is fed into the distal tip of the common lumen and the catheter is advanced into the patient over the guidewire. As the catheter advances into the patient, the guidewire enters and travels through a selected lumen of the multiple lumen proximal region of the catheter body.

Advancement of the catheter into the patient continues until the common lumen distal region lies within the blood vessel in the region of interest. The guidewire is then withdrawn into the proximal region to clear the common lumen. A suitable work element, often a rotating ultrasonic transducer, may then be advanced through the common lumen into the region of interest. Use of a catheter system of this type is described more fully in U.S. Patent application Ser. No. 07/975,769.

It is generally desirable to make the diameter of a catheter body as small as possible to allow the catheter to enter narrow and tortuous regions of the patient's vascular system. As the catheter body size is minimized, the thickness of the catheter wall is decreased and the danger that the wall will rupture may become significant.

While the danger of catheter wall failure is present in any catheter system, it may be particularly troublesome in a common lumen catheter of the type described in application Ser. No. 07/975,769. First, the common lumen is designed specifically to be small in diameter and to be positioned in particularly narrow and twisted regions of the vascular system. Second, the work element in a common lumen catheter not only rotates but also advances lengthwise through the lumen. When the rotating work element encounters a kink in the catheter body, it will impact the wall at the kink and in some cases may cause failure of the catheter body wall.

For these reasons, it would be desirable to provide an attachment for a work element that would allow the work element to track the lumen of the catheter body more reliably with less danger of puncturing the catheter wall. Such an improved tracking tip could find use in any catheter system having a work element and a tubular catheter body. It is expected, however, that such an improved tracking tip will prove particularly advantageous in a catheter system such as that described in application Ser. No. 07/975,769, where the work element is rotating, where it may be advanced longitudinally through the catheter body, and where the catheter body is particularly small in diameter.

SUMMARY OF THE INVENTION

The present invention provides an improved tracking tip for attachment to or inclusion on the distal end of a work element in a catheter system. The tracking tip will have a flexibility greater than that of the untipped work element. When the work element is advanced through the catheter body, the tracking tip will facilitate tracking of the work element through the catheter body, particularly in regions where the catheter body is sharply bent or kinked.

In preferred embodiments, the work element comprises a wound wire coil having the general configuration of a small helical spring. In some preferred embodiments, the wire coil may be tapered, i.e., the wire coil diameter may decrease in a direction distal of the work element. A tapered wire coil may be formed by wrapping an appropriate wire around a tapered mandrel. In particularly preferred embodiments, the wire coil will be formed of a wire whose diameter also decreases in the distal direction. This results in a tracking tip whose flexibility increases significantly as one moves distal of the work element.

In most cases, the tracking tip of the present invention will be fitted at its distal tip with an end member having a rounded surface substantially opposite the work element. This end member may be in the form of a spherical solder ball joined to the distal end of a wire coil or a spherical tip may be welded onto the wire coil. It may be desirable to coat this rounded end member with a non-stick material such as polytetrafluoroethylene (PTFE, sold by DuPont under the trade name Teflon) to further facilitate tracking of the tip and work element through tight bends and kinks in the catheter body.

BRIEF DESCRIPTION OF THE DRAWINGS

FIG. 7 depicts a common lumen catheter having a tracking tip according to the present invention.

FIG. 8 depicts the proximal end of a common lumen catheter system.

DESCRIPTION OF SPECIFIC EMBODIMENTS

Figure 1A:
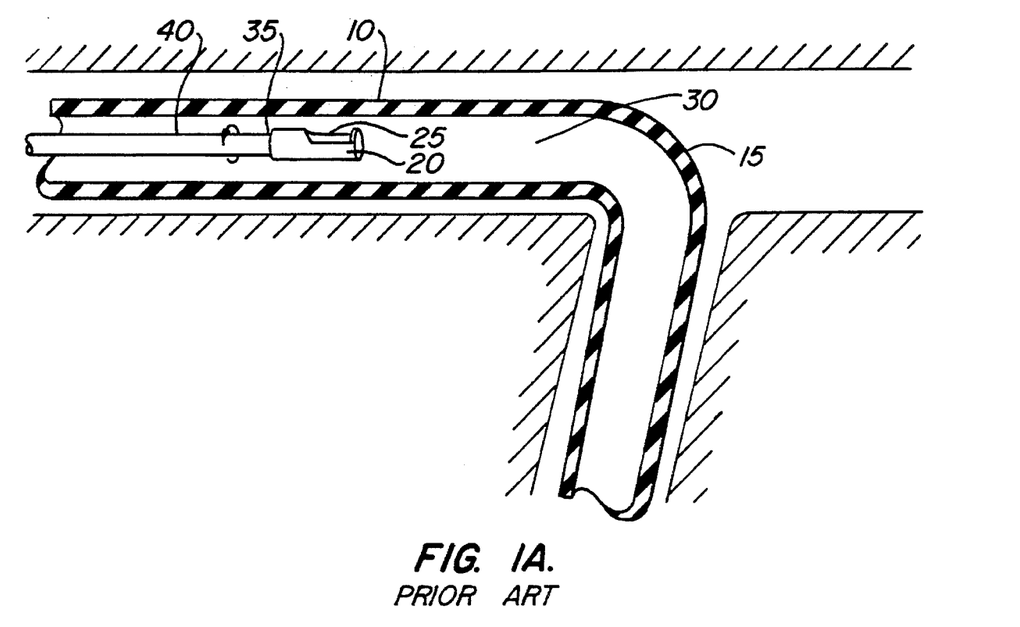
FIGS. 1A–1C depict the use of a catheter system having a conventional work element of the type known in the prior art.
Figure 1B:
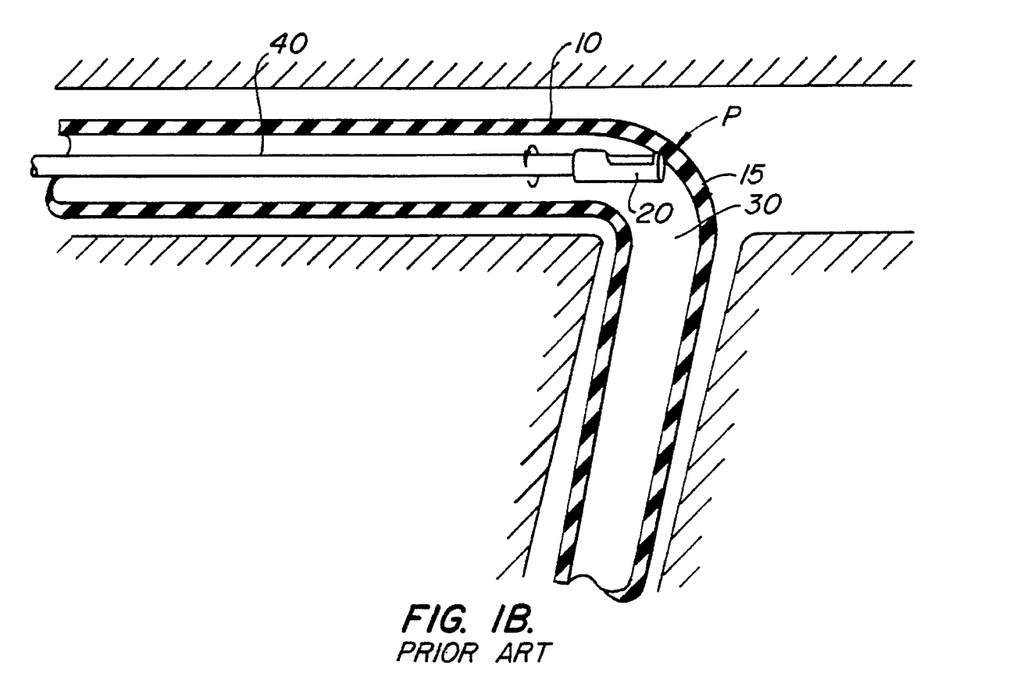
Figure 1C:
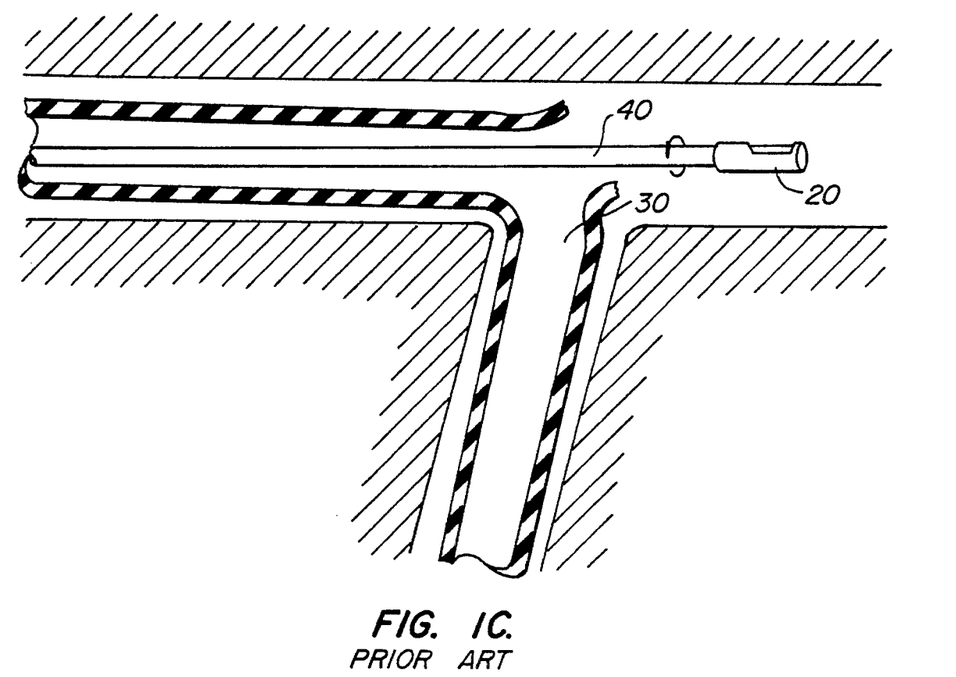

FIGS. 1A–1C depict a catheter system having a conventional work element. The system includes a catheter body 10 in the form of a flexible tubular member. FIG. 1A depicts the catheter body disposed within a branched blood vessel. The catheter body is bent sharply at a region 15 representing a sharp turn at a junction of the patient's vascular system. A rotating work element 20, which in this case includes an ultrasonic transducer 25, is being advanced through a central lumen 30 of catheter body 10 at the distal end 35 of a rotating drive shaft 40. As is known in the art, drive shaft 40 will most commonly be in the form of a twisted or braided cable but may in some cases be formed of a solid or tubular shaft of a suitable material.

As work element 20 advances further into bent region 15, the work element will come into contact with the wall of catheter body 10. Pressure between work element 20 and the wall will arise in a small localized area. This is depicted in FIG. 1B by a single arrow P, which represents the application of pressure between the work element and the wall at an initial point of contact.

As more force is applied to drive shaft 40, the pressure between work element 20 and the catheter wall may exceed the burst pressure of the wall. In that case, the wall will fail at the point of contact and the work element may protrude out of central lumen 30 into the blood vessel itself as depicted in FIG. 1C. This is potentially a very serious problem. At a minimum, the catheter system has failed and will have to be removed from the patient. Furthermore, the rotating work element and drive shaft are now exposed and may come into contact with the blood vessel wall and injure the patient.

Figure 2:
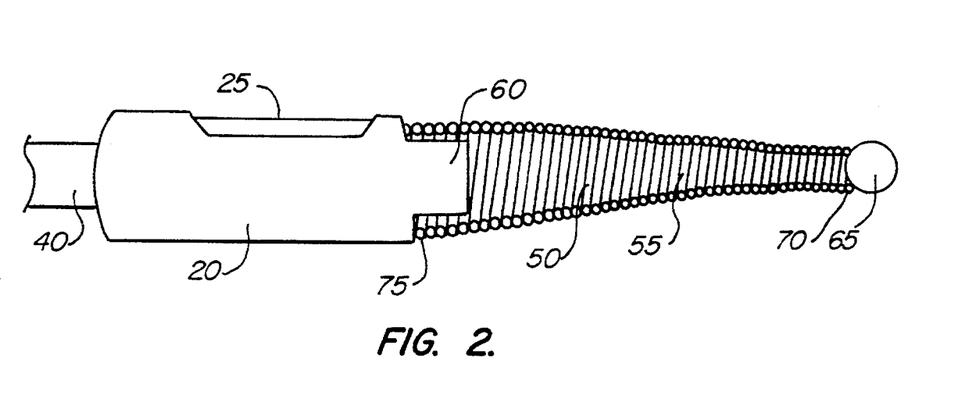
FIG. 2 depicts a work element having a tracking tip according to the present invention.

FIG. 2 depicts a work element 20 fitted with an improved tracking tip 50 according to the present invention. The embodiment depicted comprises a tapered wire coil 55 fixed to the distal tip 60 of the work element. Wire coil 55 is fitted with a solder ball 65 at its distal end 70. The work element 20 can be rotated by the drive shaft 40. Attached to a proximal end of the drive shaft 40 is a rotation coupling for removable attachment to a drive motor. When the rotation coupling is attached to the drive motor, and the drive motor is actuated, the drive shaft 40 and connected work element 20 experience rotational movement.

Wire coil 55 is welded to the work element, typically by resistance welding. Soldering or bonding with an adhesive might also be acceptable although, at present, they are considered less reliable than welding. Work element 20, wire coil 55, or both may be formed of a precipitation hardenable alloy. If this is so, the assembly may be heat treated after welding to regain the desired material properties, e.g., tensile and yield strength, that are diminished due to annealing in the weld process.

The spring-like wire coil 55 provides tracking tip 50 with a degree of flexibility not present in an unmodified work element. The wire coil may be formed by wrapping an appropriately chosen wire around a tapered mandrel to achieve a wire coil whose diameter decreases distal to the work element. In preferred embodiments, the diameter of the wrapped wire itself decreases in the distal direction. In these embodiments, a wire of decreasing diameter is wrapped around a mandrel of decreasing diameter to form a wire coil 55 with further enhanced flexibility in the region of distal end 70.

The construction and dimensions and even the material used to construct the tracking tip of the claimed invention may vary significantly depending on the circumstances under which it is to be used. For example, the tracking tip need not be made in all cases of a wound wire coil. In some cases the tracking tip could be made of a solid but flexible metal member or of a polymeric material of appropriate flexibility. For the purpose of illustration, however, the construction and dimensions of a particularly preferred embodiment will be described in detail below.

The configuration described has been found useful as an addition to a work element in the form of an ultrasonic imaging transducer assembly having an outside diameter of 0.029 inches. Referring again to FIG. 2, the particular embodiment comprises a tracking tip 50, which is 0.300 inches in length from proximal end 75 to distal end 70. Wire coil 55 tapers from 0.029 inches in diameter at proximal end 75 (to match the diameter of work element 20) down to a diameter of 0.012 inches at distal end 70. The wire coil is capped at distal end 70 by a spherical solder ball 65 with a diameter between 0.022 and 0.018 inches. In a preferred embodiment, the wire that forms the wire coil is itself of decreasing diameter. In this embodiment, the wire has a diameter of 0.006 inches at proximal end 75 and a diameter of 0.003 inches at distal end 70.

Figure 3A:
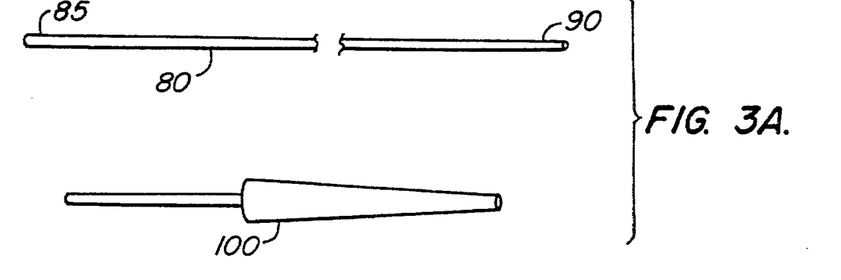
FIGS. 3A and 3B depict the steps for winding a wire around a mandrel to form a wire coil suitable for use in a tracking tip according to the present invention.
Figure 3B:
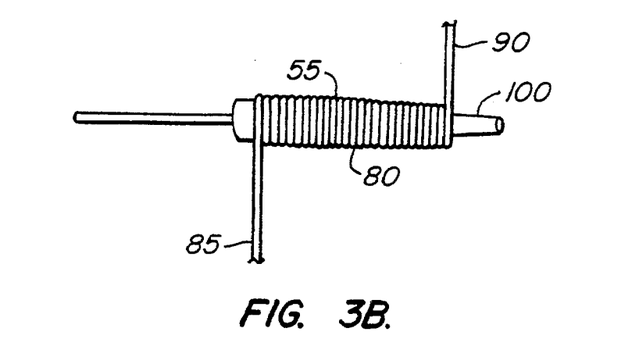

The tracking tip may be formed as depicted in FIGS. 3A and 3B. First, a wire 80 of appropriate dimension and material is selected. If desired, the wire may taper, or decrease in diameter, from a proximal end 85 to a distal end 90. An appropriate (usually tapered) mandrel 100 is also selected. Wire 80 and mandrel 100 are depicted in FIG. 3A. Wire coil 55 is formed by wrapping wire 80 around mandrel 100 as depicted in FIG. 3B. Finally, proximal and distal wire ends 85 and 90 are clipped and the wire coil is ground smooth at its proximal and distal ends.

Figure 4A:
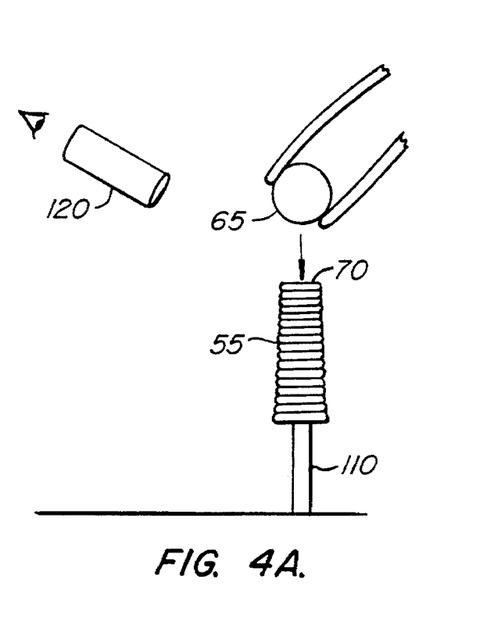
FIGS. 4A and 4B depict the steps for joining a rounded end member in the form of a solder ball to the distal end of the wire coil.
Figure 4B:
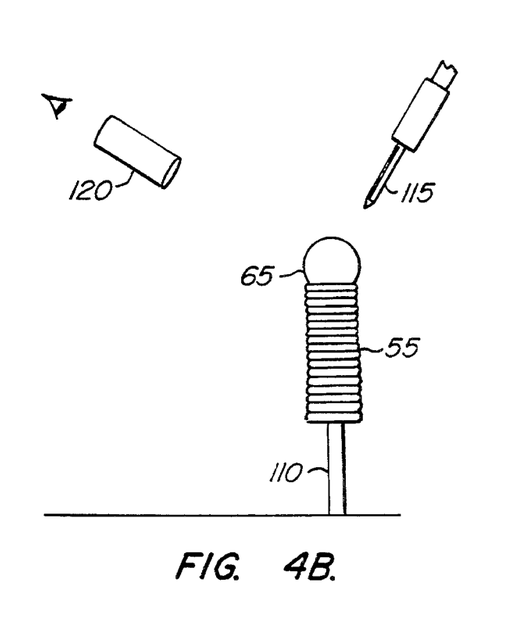

A solder ball may be fixed to the distal end of the wire coil as depicted in FIGS. 4A and 4B. After the wire ends are clipped and the wire coil ends are ground smooth, wire coil 55 is placed on a holder 110 with distal end 70 facing up as depicted in FIG. 4A. Then a solid solder ball 65 of appropriate diameter is dipped into and coated with an appropriate flux material. Solid solder ball 65 is placed onto distal end 70 of coil 55. When the hot tip of a soldering iron 115 is touched to the solder ball, surface tension causes the rough solder ball to flow to form a smooth, near-perfect sphere as depicted in FIG. 4B. As indicated in FIGS. 4A and 4B, a low-power microscope 120 may facilitate manipulation and heating of the wire coil and solder ball.

If desired, the solder ball may be coated after cooling with a suitable lubricant or a non-stick material such as polytetrafluoroethylene (PTFE), a material sold by DuPont under the trade name Teflon. A lubricant or non-stick coating on the solder ball may further improve tracking of the work element through tight bends or kinks in the catheter body.

Figure 5A:
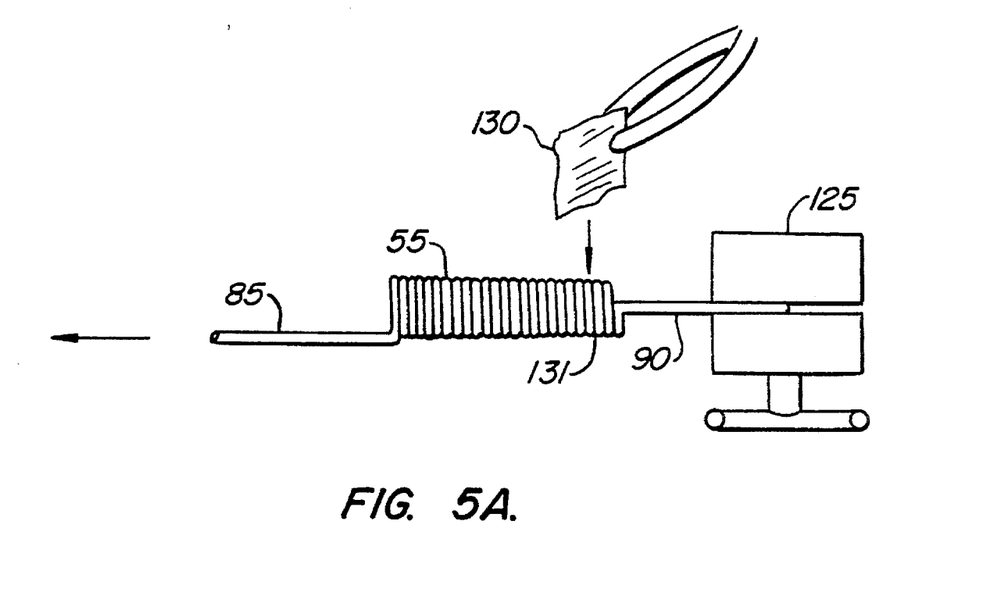
FIGS. 5A and 5B depict a method for forming an improved bond between the solder ball and wire coil depicted in FIGS. 4A and 4B.
Figure 5B:
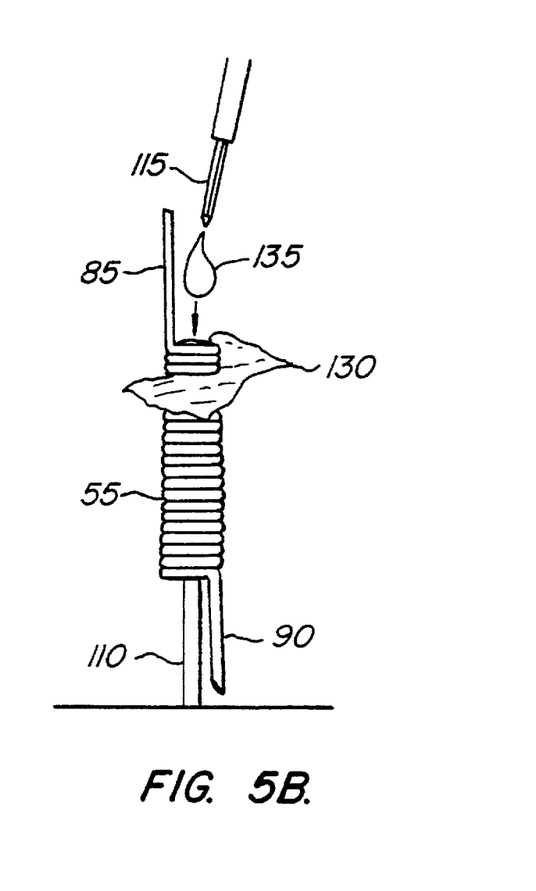

While the procedure described above will generally produce an acceptable bond between the solder ball and the wire coil, prototype testing has shown that the strength of the bond between the coil and the solder ball may be significantly increased if the first few turns at the distal end of the wire coil are "pre-tinned," i.e., filled with solder prior to attachment of the ball. This may be done as shown in FIGS. 5A and 5B. After the wire coil is wrapped on the tapered mandrel, but before the wire ends are clipped, distal wire end 90 of wire coil 55 is placed in a small clamp or vise 125. By pulling gently on proximal wire end 85, gaps may be opened between the individual turns of wire coil 55.

A small piece of polyimide film 130 (available from DuPont under the trade name "Kapton") can then be slipped as seen in FIG. 5A into a gap in the wire coil at a desired location, e.g., between the third and fourth coils of the distal end (a position indicated as 131 in FIG. 5A).

As depicted in FIG. 5B, wire coil 55 is then placed on holder 110 with polyimide film 130 still in place within the coil. Solder 135 is applied to distal end 70 of the wire coil and allowed to fill the interior of the coils down to the polyimide film. After the solder hardens, the wire coil is placed back in the vise and the polyimide film removed.

Wire ends 85 and 90 are then clipped and the wire coil ends are ground smooth. The procedure is completed by the performing the steps depicted in FIGS. 4A and 4B and described above. In this embodiment, however, when the solder ball is heated the solder of the ball merges and joins with the solder prepositioned within the coils. This results in a stronger bond compared to the embodiment in which the solder ball alone is applied directly to the coils.

Figure 6A:
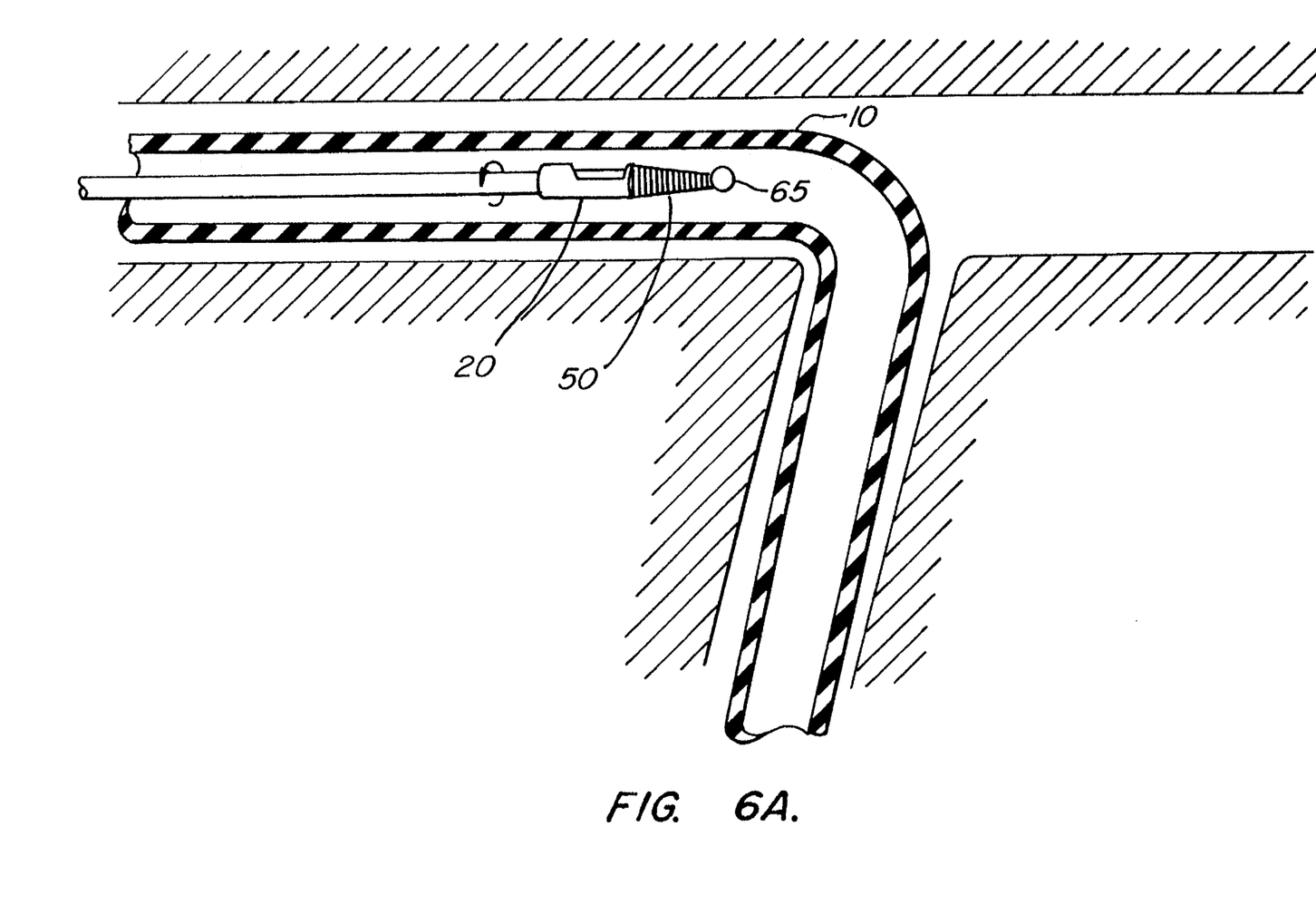
FIGS. 6A–6C depict a catheter system having a tracking tip according to the present invention disposed within a blood vessel within a patient.
Figure 6B:
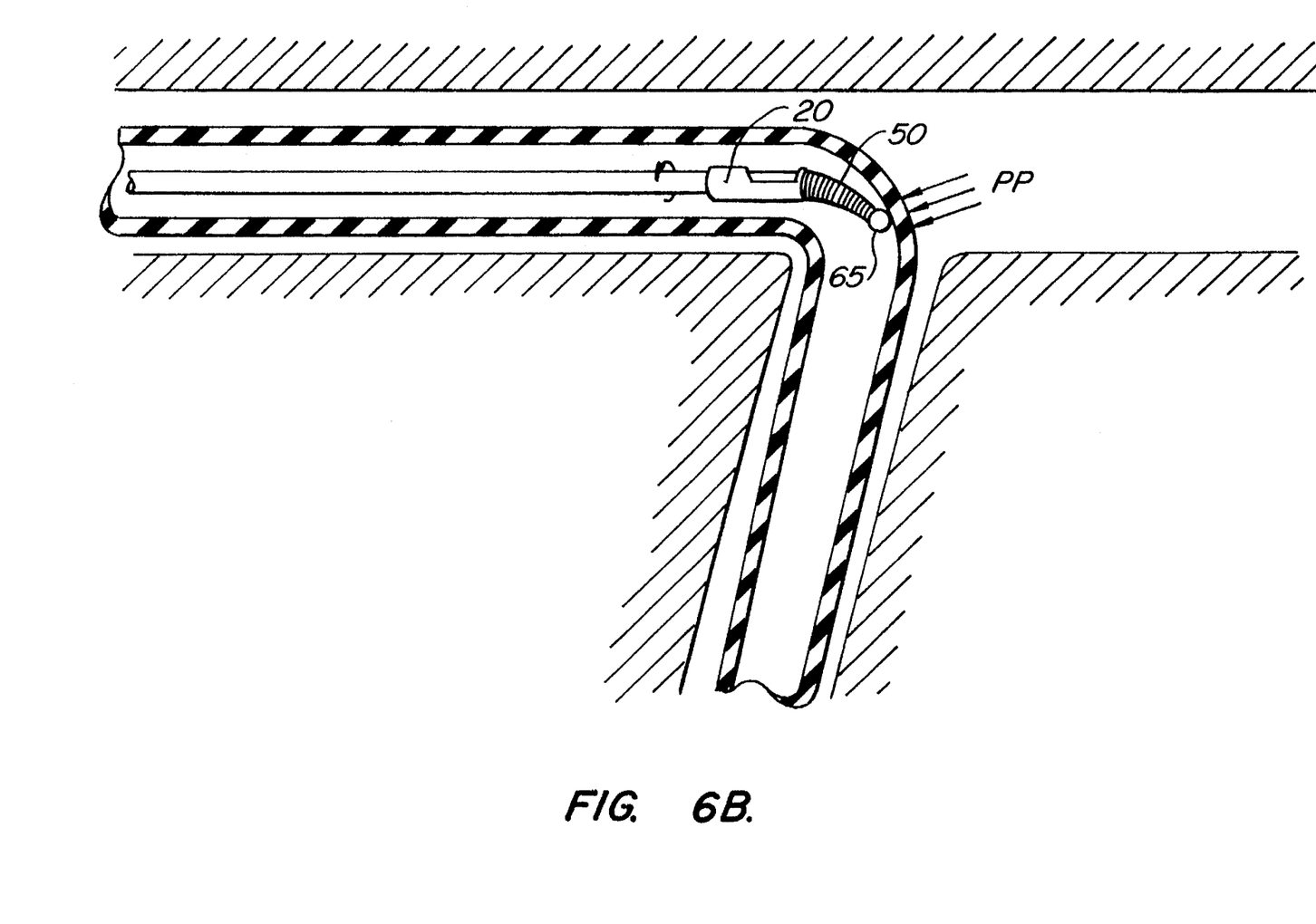
Figure 6C:
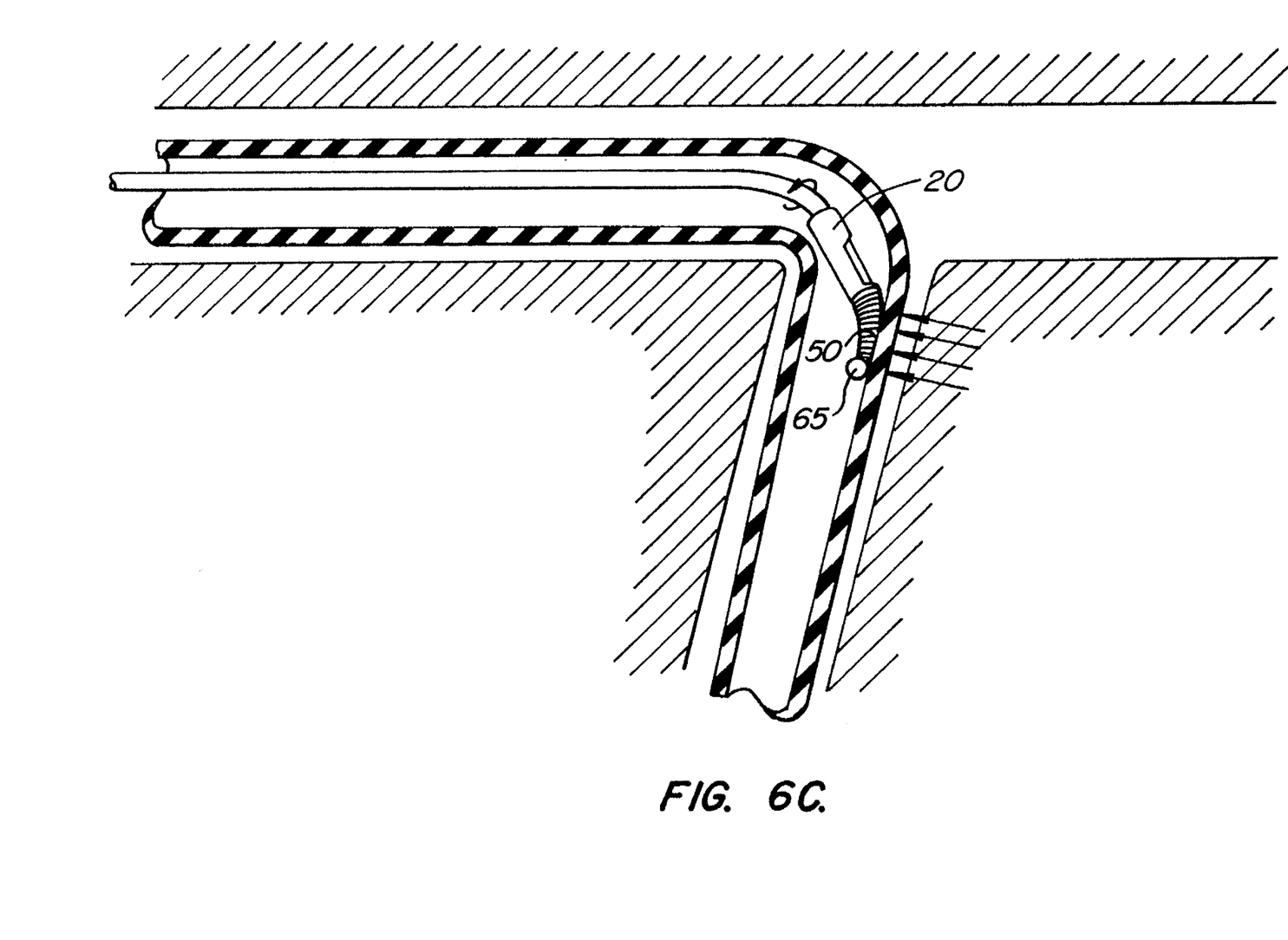

A tracking tip according to the present invention improves tracking of the work element through the catheter body as depicted in FIGS. 6A–6C. FIG. 6A depicts a catheter system having a work element 20 fitted with an improved tracking tip 50 according to the present invention. As the work element advances through catheter body 10, tracking tip 50 contacts the interior wall of the catheter body as depicted in FIG. 6B. Near the point of initial contact, the pressure between the tracking tip and the wall is distributed over a portion of the rounded surface of solder ball 65. This distributed pressure is indicated symbolically by the presence of multiple pressure arrows PP in FIG. 6B.

Because the same force is distributed over a larger area of initial contact, and furthermore because the tracking tip is flexible, the pressure exerted on the catheter wall by the tracking tip will not exceed the burst pressure of the wall and the wall will not rupture. Instead, the tracking tip guides the work element smoothly around the bend in the catheter body as shown in FIG. 6C. Tracking of the tip around the bend may be further enhanced if the solder ball, the catheter body wall, or both, are coated with a suitable lubricant or non-stick material as mentioned above.

FIG. 7 and FIG. 8 illustrate an embodiment of a common lumen catheter system having a tracking tip according to the present invention. A catheter system of this type is more fully describe in application Ser. No. 07/975,769. As shown, a common lumen catheter 150 includes a flexible catheter body 151 having a distal region 155 and a proximal region 160. The distal region 155 includes a single lumen 156. The proximal region 160 includes a first lumen 161 and a second lumen 162, both of which are connected to and in communication with the single distal lumen 156. The first lumen 161 carries a movable guidewire 163.

Drive shaft 40 is reciprocatably disposed within the second lumen 162. As illustrated in FIG. 7, work element 20 is secured to the distal end of drive shaft 40. The improved tracking tip 50 is fixed to the distal end of the work element 20.

As illustrated in FIG. 8, common lumen catheter 150 further includes a proximal housing 170 secured to the proximal end of the catheter body 151. The housing 170 includes a spindle 172 at the proximal terminal end of the drive shaft 40 for coupling to a motor drive.

Proximal housing 170 further includes a lever 171 which is attached to the drive shaft 40. Lever 171 permits the user to selectively reciprocate the work element 20 between a retracted position (in the second lumen 162 of proximal region 160) and an extended position (in the single distal lumen 156, as shown in FIG. 7). As the work element is extended, the improved tracking tip 50 allows the work element to track the lumen of the common lumen catheter body more reliably and with less danger of puncturing the catheter wall, as described above.

The present invention has been discussed in some detail and specific embodiments described. Other useful embodiments and applications will readily occur to those skilled in the art. For example, although the improved tracking tip of the present invention has been described principally in connection with catheters having ultrasonic imaging transducers as work elements, other work elements may benefit from the improved tracking and decreased risk of puncture provided by the present invention. Additionally, the precise dimensions and materials used to construct the tracking tip may vary significantly depending upon the intended application. The scope of the invention should therefore be determined not with respect to the particular embodiments described but rather by referring to the appended claims along with the full extent of equivalents to which they are rightfully entitled.

What is claimed is:

1. A catheter system comprising:

a catheter body comprising a flexible tubular member having a lumen extending therethrough;

a drive shaft having proximal and distal ends and a rotation coupling for removable attachment to a drive motor disposed at the proximal end, the drive shaft being rotatably disposed within the lumen of the catheter body;

a work element fixed to the distal end of the drive shaft; and a tracking tip fixed to the work element substantially opposite the drive shaft and disposed within the lumen of the catheter body, the tracking tip comprising a flexible member having a flexibility greater than that of the work element, wherein the flexibility of the tracking tip increases from a proximal member end at the work element to a distal end.

2. The catheter system of claim 1, wherein the drive shaft and work element are movable within the lumen along the length of the catheter body.

3. The catheter system of claim 1, wherein the work element comprises an ultrasonic imaging transducer.

4. The catheter system of claim 1, wherein the flexible member is formed of a wire coil.

5. The catheter system of claim 4, further comprising:

a quantity of solder disposed within the wire coil at an end opposite the work element; and a substantially spherical solder ball fixed to the wire coil at the end opposite the work element and joined with the solder disposed within the wire coil.

6. The catheter system of claim 1, further comprising an end member fixed to the flexible member substantially opposite the work element, the end member having an exposed rounded surface substantially opposite the flexible member.

7. The catheter system of claim 6, wherein the end member comprises a substantially spherical solder ball.

8. The catheter system of claim 6, further comprising a non-stick material applied to the rounded surface of the end member.

9. The catheter system of claim 8, wherein the non-stick material is comprised of polytetrafluoroethylene.

10. The catheter system as in claim 1, wherein the work element is an ultrasonic imaging transducer assembly having a defined outside diameter, and wherein the flexible member has a proximal end and a distal end, the proximal end being fixed to the work element, and wherein the proximal end of the flexible member has a diameter that conforms substantially to the defined diameter of the transducer assembly.

11. A catheter system comprising:

a catheter body comprising a flexible tubular member having a lumen extending therethrough;

a drive shaft having proximal and distal ends and a rotation coupling for removable attachment to a drive motor disposed at the proximal end, the drive shaft being rotatably disposed within the lumen of the catheter body;

a work element fixed to the distal end of the drive shaft; and a tracking tip fixed to the work element substantially opposite the drive shaft and disposed within the lumen of the catheter body, the tracking tip comprising a flexible member having a flexibility greater than that of the work element;

wherein the flexible member is formed of a wire coil; and wherein the wire coil is formed of a wire of non-uniform diameter.

12. The catheter system of claim 11, wherein the wire diameter decreases from an end joined to the work element to an end opposite the work element.

13. An improved common lumen catheter system of the type comprising a flexible catheter body having a proximal and a distal region, the proximal region having at least two lumens and the distal region having a common lumen connected to and in communication with both lumens of the proximal region; a drive shaft having proximal and distal ends, the drive shaft disposed within one lumen of the proximal region and capable of being advanced into the common lumen; and a work element fixed to the distal end of the drive shaft; wherein the improvement comprises:

a tracking tip fixed to the work element substantially opposite the drive shaft, the tracking tip comprising a flexible member having a proximal member end adjacent the work element and a distal member end opposite the work element, wherein the flexible member has a flexibility greater than that of the work element, and wherein the flexibility increases from the proximal member end to the distal member end.

14. The catheter system of claim 13, wherein the flexible member is formed of a wire coil.

15. The catheter system of claim 13, further comprising an end member fixed to the flexible member substantially opposite the work element, the end member having an exposed rounded surface.

16. A tracking tip in combination with a work element fixed to a drive shaft in a catheter system, the tracking tip comprising:

a flexible member having a flexibility greater than that of the work element, the flexible member extending from the work element in a direction substantially opposite the drive shaft, wherein the work element is an ultrasonic imaging transducer assembly having a defined outside diameter, and wherein the flexible member has a proximal end and a distal end, the proximal end being attached to the work element, wherein the flexibility increases progressively from the proximal end to the distal end, and wherein the proximal end of the flexible member has a diameter that conforms substantially to the defined diameter of the transducer assembly.

17. The tracking tip of claim 16, wherein the flexible member is formed of a wire coil.

18. The tracking tip of claim 17, wherein the wire coil decreases in diameter in a direction away from the work element.

19. The tracking tip of claim 17, wherein the wire coil is formed of a wire of non-uniform diameter.

20. The tracking tip of claim 19, wherein the wire diameter decreases from an end joined to the work element to an end opposite the work element.

21. The tracking tip of claim 17, further comprising:

a quantity of solder disposed within the wire coil at an end opposite the work element; and a substantially spherical solder ball fixed to the wire coil at the end opposite the work element and joined with the solder disposed within the wire coil.

22. The tracking tip of claim 16, further comprising an end member fixed to the flexible member substantially opposite the work element, the end member having an exposed rounded surface.

23. The tracking tip of claim 22, wherein the end member comprises a substantially spherical solder ball.

24. The tracking tip of claim 22, further comprising a non-stick material applied to the rounded surface of the end member.

25. The tracking tip of claim 24, wherein the non-stick material is comprised of polytetrafluoroethylene.

26. The tracking tip of claim 16, wherein the tracking tip is formed at least in part of a precipitation hardenable metal alloy.

* * * * *